(12) United States Patent
Dastillung et al.

(10) Patent No.: US 9,950,969 B2
(45) Date of Patent: Apr. 24, 2018

(54) METHOD FOR THE PRODUCTION OF BUTADIENE FROM ETHANOL IN ONE LOW-WATER- AND LOW-ENERGY-CONSUMPTION REACTION STEP

(71) Applicants: IFP Energies Nouvelles, Rueil-Malmaison (FR); Compagnie Generale des Etablissements Michelin, Clermont-Ferrand (FR); Michelin Recherche et Technique S.A., Granges-Paccot (CH)

(72) Inventors: Rejane Dastillung, Lyons (FR); Beatrice Fischer, Lyons (FR); Marc Jacquin, Lyons (FR); Raphael Huyghe, Saint Andeol le Chateau (FR)

(73) Assignees: IFP Energies Nouvelles, Rueil-Malmaison (FR); Compagnie Generale des Etablissements Michelin, Clermont-Ferrand (FR); Michelin Recherche et Technique S.A., Granges-Paccot (CH)

( * ) Notice: Subject to any disclaimer, the term of this patent is extended or adjusted under 35 U.S.C. 154(b) by 0 days.

(21) Appl. No.: 15/512,183

(22) PCT Filed: Sep. 17, 2015

(86) PCT No.: PCT/EP2015/071362
§ 371 (c)(1),
(2) Date: Mar. 17, 2017

(87) PCT Pub. No.: WO2016/042096
PCT Pub. Date: Mar. 24, 2016

(65) Prior Publication Data
US 2017/0267604 A1 Sep. 21, 2017

(30) Foreign Application Priority Data

Sep. 19, 2014 (FR) .................................... 14 58860

(51) Int. Cl.
*C07C 1/20* (2006.01)
*C07C 2/40* (2006.01)
(Continued)

(52) U.S. Cl.
CPC .................. *C07C 2/40* (2013.01); *B01D 3/14* (2013.01); *B01D 11/04* (2013.01); *C07C 2/867* (2013.01); *F28D 15/02* (2013.01)

(58) Field of Classification Search
CPC ......... C07C 1/20; C07C 11/167; C07C 11/16; C07C 1/207; C07C 1/2072;
(Continued)

(56) References Cited

U.S. PATENT DOCUMENTS 2,403,743 A 7/1946 Hitchcock et al.
8,921,635 B2 * 12/2014 Ordomskiy ............... C07C 1/20
585/607

OTHER PUBLICATIONS

International Search Report dated Dec. 3, 2015 issued in corresponding PCT/EP2015/071362 application (2 pages).

* cited by examiner

*Primary Examiner* — Sharon Pregler
(74) *Attorney, Agent, or Firm* — Millen, White, Zelano and Branigan, P.C.

(57) ABSTRACT

The invention concerns a process for the production of butadiene from an ethanol feed comprising at least 80% by weight of ethanol, comprising a step for conversion of ethanol to acetaldehyde, a step for the extraction of butadiene, a step for scrubbing gaseous by-products with water, a step for eliminating impurities and brown oils, a step for treating effluents, a first butadiene purification step, and a
(Continued)

subsequent butadiene purification step, said ethanol feed being supplied to said butadiene extraction step, the arrangement of the steps and recycles allowing the recycles to be maximized and allowing the water and energy consumption to be minimized.

15 Claims, 4 Drawing Sheets

(51) Int. Cl.
    *B01D 11/04*     (2006.01)
    *B01D 3/14*     (2006.01)
    *C07C 2/86*     (2006.01)
    *F28D 15/02*     (2006.01)

(58) Field of Classification Search
    CPC ............ C07C 2523/50; C07C 2523/52; C07C 2523/63; C07C 2523/64; C07C 2523/644; C07C 2523/72; C07C 2/40; C07C 2/867; B01D 11/04; B01D 3/14
    See application file for complete search history.

METHOD FOR THE PRODUCTION OF BUTADIENE FROM ETHANOL IN ONE LOW-WATER- AND LOW-ENERGY-CONSUMPTION REACTION STEP

FIELD OF THE INVENTION

The invention relates to a process for the production of butadiene from ethanol or from an ethanol/acetaldehyde mixture operating in one reaction step.

PRIOR ART

Processes for the production of butadiene from ethanol were developed in particular by the Russians, based on work by Lebedev in the 1920s (process with 1 reaction step), and by the Americans during the second world war from the work by Ostromilenski (process with 2 reaction steps—dehydrogenation of ethanol to form acetaldehyde, then production of butadiene from an ethanol/acetaldehyde mixture).

The process, in its Lebedev version, has a conversion per pass substantially below 50%, which implies a lot of recycling, and it is difficult to precisely adjust the ethanol/acetaldehyde ratio at the inlet to the reaction section.

Another problem with the process is the production of a large variety of all sorts of impurities: saturated, unsaturated and aromatic hydrocarbons, but also oxygen-containing products such as alcohols, phenols, aldehydes, ketones, acids, esters, ethers or acetals.

Certain of these by-products, both gaseous and liquid under normal temperature and pressure conditions, are generated in significant quantities. Gaseous by-products that may be cited include hydrogen, carbon monoxide, carbon dioxide, $C_1$-$C_4$ alkanes and olefins, and methyl ethyl ether. Liquid by-products that may be cited include pentenes, pentadienes, diethyl ether, ethyl vinyl ether, hexenes, hexadienes, butanal, crotonaldehyde, ethyl acetate, diethyl acetal, butanol, hexanol and acetic acid. These gaseous and liquid by-products are problematic as regards obtaining butadiene complying with specifications, but also because recycling them to the reaction steps with ethanol and acetaldehyde induces a reduction in the overall yield from the unit. Extracting them substantially complicates the separation process.

Other by-products are generated in tiny amounts. In the remainder of the document, the term "brown oils" will be used to designate the set of thousands of hydrocarbon and oxygen-containing compounds produced in the reaction sections with boiling points which are between that of ethanol and up to 600° C. These brown oils have the particular feature of being soluble in ethanol but insoluble in water. Particularly when they are not diluted by a large excess of ethanol, they can clog together and block up the equipment. Furthermore, these brown oils are problematic in the distillation column which separates the water produced by the reaction and unconverted ethanol. In fact, these brown oils are soluble in the water-ethanol effluent supplying said distillation column, and insoluble in the residue essentially constituted by water. A phase separation thus occurs in this column, considerably reducing the efficiency of the separation. The brown oils are difficult to eliminate within the process because they are constituted by thousands of compounds having very different physico-chemical properties. A fraction of these brown oils thus accumulates within the process, engendering a drop in its operational efficiency after a few days or weeks at best. Thus, it is periodically necessary to purge certain streams, resulting in a loss of ethanol and acetaldehyde thereby degrading the overall yield of the process at a cost which would be prohibitive today.

Because of the numerous impurities produced by the process, the purification of butadiene is complex. It calls upon a combination of numerous unitary operations such as scrubs, simple and extractive distillations. The prior art recommends the use of extractive distillations using a solvent, bis(2-chloroethyl)ether (Chlorex), which is now banned because of its high toxicity. It is important to note that the specifications for butadiene are now extremely severe because of the sensitivity of butadiene polymerization catalysts. Reproducing the prior art concatenation of unitary operations would thus mean that current specifications would not be met. As an example, the specification for acetaldehyde (an intermediate reagent for the production of butadiene) in butadiene have changed from 1000 ppm to less than 10 ppm today. The work "Synthetic rubber from alcohol", (A. Talalay, M. Magat, 1945), provides a general view of the process which has been developed.

Aim and Advantage of the Invention

The invention provides a process for the production of butadiene from an ethanol feed comprising at least 80% by weight of ethanol, comprising at least:
A) a step for converting the ethanol into butadiene, comprising at least one reaction section supplied with at least the ethanol effluent and a fraction of the acetaldehyde effluent obtained from step E), operated at a pressure in the range 0.1 to 1.0 MPa and at a temperature in the range 300° C. to 400° C. in the presence of a catalyst, and a separation section for separating the effluent from said reaction section into at least a gaseous effluent and a liquid effluent, the fraction of the acetaldehyde effluent obtained from step E) which is not supplied to said reaction section constituting the purge stream;
B) a step for extracting butadiene, comprising at least one compression section compressing said gaseous effluent obtained from step A) to a pressure in the range 0.1 to 1.0 MPa, a gas-liquid scrubbing section supplied with an ethanol stream constituted by said ethanol feed for the process and/or a fraction of the ethanol effluent obtained from step E) and with said compressed gaseous effluent, in which the gas is supplied at a temperature in the range 10° C. to 60° C., and the liquid is supplied at a temperature in the range 20° C. to –30° C., and producing at least one ethanol stream enriched in butadiene and a gaseous effluent of by-products, and a distillation section supplied with said ethanol stream enriched in butadiene and producing an unrefined butadiene effluent and an ethanol/acetaldehyde/water residue, said distillation section being operated at between 0.1 and 1 MPa;
C) a step for scrubbing gaseous by-products with water supplied with the effluent of gaseous by-products obtained from step B), as well as with a fraction of the water-rich effluent obtained from said step E) and producing at least one alcohol-containing water effluent;
D) a step for eliminating impurities and brown oils, supplied with at least the ethanol/acetaldehyde/water effluent obtained from step B), and with a fraction of the water effluent obtained from step E), and producing at least one water/ethanol/acetaldehyde raffinate, a light brown oil effluent and a heavy brown oil effluent;
E) an effluent treatment step supplied with at least the water/ethanol/acetaldehyde raffinate obtained from step D), and producing at least one ethanol effluent, an acetaldehyde effluent and a water effluent;

F) a first butadiene purification step comprising at least one gas-liquid scrubbing section the bottom of which is supplied with the unrefined butadiene effluent obtained from B) and the head of which is supplied with a stream of water which may be a stream of water with an origin external to said butadiene production process and/or a fraction of the water effluent obtained from step E), said scrubbing section producing an overhead pre-purified butadiene effluent and a spent water effluent from the bottom;

G) a subsequent butadiene purification step supplied with at least said pre-purified butadiene effluent obtained from said step F), and producing at least one purified butadiene effluent.

The Applicant has identified an arrangement of unitary operations which can be used to overcome the numerous disadvantages of the prior art. In particular, the arrangement of unitary operations of the invention can be used to eliminate gaseous impurities, liquid impurities and brown oils while minimizing the loss of ethanol and acetaldehyde, thereby improving the overall yield of the unit while reducing the overall flow of water necessary for the separation steps and obtaining a very pure butadiene. The large reduction in the overall flow of water means that the energy consumption of the process can be reduced, along with the dimensions of the separation equipment.

DETAILED DESCRIPTION OF THE INVENTION

Feed

The ethanol feed used in the process of the invention may be of any origin—fossil, plant or animal—, and in particular from processes for the production of ethanol from plant resources. Said feed comprises at least 80% by weight of ethanol, preferably at least 90% by weight, and preferably at least 93% by weight. Highly preferably, said ethanol feed satisfies EN 15376 ethanol fuel specifications.

Step A) for the Conversion of Ethanol into Butadiene

In accordance with the invention, a step A) for converting ethanol into butadiene comprises at least one reaction section and a separation section for separating the effluent from said reaction section into at least a gaseous effluent and a liquid effluent. Said reaction section of said step A) is supplied with the ethanol effluent and the acetaldehyde effluent obtained from step E) for the treatment of the effluents, and optionally with a fraction of said ethanol feed. Said step A) may also be supplied with an external acetaldehyde stream.

The ratio of ethanol to acetaldehyde at the inlet to the reaction section is adjusted by controlling the fraction of the acetaldehyde effluent obtained from said step E) supplying the step A). Thus, with the process of the invention, control of the ethanol to acetaldehyde ratio in said reaction section is rendered easy. This ratio is adjusted to the desired value by the skilled person as a function of the catalyst employed.

The fraction of the acetaldehyde effluent obtained from said step E) which is not sent to the reaction section constitutes a stream termed the purge. The acetaldehyde and ethyl acetate contained in the purge could be transformed in a dedicated hydrogenation step in order to produce ethanol which would then be sent to said reaction section of said step A). It may also be treated in a dedicated reaction step containing a catalyst of the silica type with a tantalum, zirconium oxide in order to produce butadiene, operated at a temperature in the range 300° C. to 400° C. and at a pressure in the range 0.1 to 1.0 MPa. Preferably, the purge flow rate is zero and all of the ethanol/acetaldehyde effluent obtained from said step E) is sent to the reaction section.

Said reaction section can be used to convert a portion of the ethanol/acetaldehyde mixture into at least butadiene. It is operated in the presence of a catalyst which is well known to the skilled person, for example a catalyst of the silica type with a magnesium oxide, at a temperature in the range 300° C. to 400° C., preferably in the range 320° C. to 370° C. and at a pressure in the range 0.1 to 1.0 MPa, preferably in the range 0.1 to 0.5 MPa, more preferably in the range 0.1 to 0.3 MPa. The selectivity for transformation of the ethanol/acetaldehyde mixture is preferably more than 20%, more preferably more than 25%, highly preferably more than 50%. The term "selectivity" means the molar ratio of the flow rate of butadiene in the effluent from said reaction section over the flow rate of ethanol and acetaldehyde consumed in said reaction section. The conversion for the transformation of the ethanol/acetaldehyde mixture is preferably more than 40%, preferably more than 50%, more preferably more than 60%. The term "conversion" means the molar ratio of the flow rate of ethanol and acetaldehyde in the effluent from said reaction section over the flow rate of ethanol and acetaldehyde in the supply to said reaction section.

In order to maximize the conversion of ethanol and acetaldehyde and the selectivity for butadiene, the compositions at the inlet to the reaction section are adjusted as a function of the selected catalyst.

The effluent for said reaction section still comprises ethanol, as well as numerous impurities produced with the butadiene, including ethylene, propylene, diethyl ether (DEE), ethyl acetate, butanol, hexanol, butenes, pentenes, pentadienes, hexenes and hexadienes. It is supplied to said separation section of said step A).

Said separation section is intended to extract the incondensable constituents of the liquid effluent. It produces a gaseous effluent which principally contains butadiene, hydrogen, ethanol, acetaldehyde and light hydrocarbons, and a liquid effluent which principally contains water, ethanol, acetaldehyde and heavy hydrocarbons.

Said separation section employs gas-liquid separation means which are known to the skilled person. Preferably, a gas-liquid separator is used which is operated at a pressure in the range 0.1 to 0.3 MPa and at a temperature in the range 10° C. to 60° C.

Butadiene Extraction Step B)

In accordance with the invention, a step B) for extraction of butadiene comprising at least one compression section, a gas-liquid scrubbing section and a distillation section is supplied with at least said gaseous effluent obtained from said step A), optionally with said liquid effluent obtained from step A) and with an ethanol stream constituted by said ethanol feed for the process and/or a fraction of the ethanol effluent obtained from step E). Said step B) produces at least one effluent of gaseous by-products, an unrefined butadiene effluent and an ethanol/acetaldehyde/water effluent.

Said ethanol stream supplying step B) comprises at least 80% by weight of ethanol, preferably at least 90% by weight, and more preferably at least 93% by weight. Said ethanol stream supplying step B) may contain methanol, water, ethyl acetate, butanol and hexanol. Preferably, said ethanol stream supplying step B) comprises less than 10% by weight of acetaldehyde, preferably less than 5% by weight, and more preferably less than 1% by weight. Preferably, said ethanol stream supplying step B) comprises less than 20% by weight of water, preferably less than 5% by weight, more preferably less than 1% by weight.

In another preferred arrangement, said ethanol stream is constituted by a fraction of the ethanol effluent obtained from effluent treatment step E).

The use of an ethanol stream containing little or no acetaldehyde minimizes the entrainment of acetaldehyde in said effluent of gaseous by-products withdrawn from the head of said gas-liquid scrubbing section, reducing the losses in the overall yield of the process, as well as the necessary flow rate of scrubbing water in step C) for scrubbing the gaseous by-products with water.

The gaseous effluent obtained from step A) is compressed in said compression section to a pressure in the range 0.1 to 1.0 MPa, preferably in the range 0.1 to 0.7 MPa, and preferably in the range 0.2 to 0.5 MPa. The effect of this compression is on the one hand to reduce the volume flow rate of gas, and on the other hand to improve the downstream scrubbing efficiency. The compressed gaseous effluent is then cooled to a temperature in the range 10° C. to 60° C., preferably in the range 30° C. to 40° C.

Said gas-liquid scrubbing section of step B) comprises a scrubbing column with an overhead supply of said ethanol stream supplying step B), and with a bottom supply of said compressed and cooled gaseous effluent, and produces the gaseous by-products as an overhead effluent and a bottom butadiene-enriched ethanol stream which is supplied to said distillation section of step B).

Said ethanol stream supplying step B) is cooled before being supplied to the head of said gas-liquid scrubbing column of the scrubbing section at a temperature in the range 20° C. to −30° C., preferably in the range 5° C. to −15° C. The importance of cooling said ethanol stream is to improve the performance of the scrubbing operation by minimizing the entrainment of ethanol and acetaldehyde in said effluent of gaseous by-products. Thus, all of the butadiene present in the compressed and cooled gaseous effluent obtained from step A) is scrubbed and the effluent vapour of by-products withdrawn from the head of said gas-liquid scrubbing section is free from butadiene.

Minimizing the acetaldehyde entrainment in said effluent of gaseous by-products can incidentally substantially reduce the flow rate of water required in step C) for scrubbing the gaseous by-products with water, the aim of which is to recover ethanol and any traces of acetaldehyde entrained in the effluent of gaseous by-products withdrawn from the head of the ethanol scrubbing section of step B).

In a particular arrangement, the ethanol stream enriched in butadiene withdrawn from the bottom of said gas-liquid scrubbing section of step B) is mixed with the liquid effluent obtained from step A) so as to form the supply for said distillation section of step B).

In another particular arrangement, the ethanol stream enriched in butadiene withdrawn from the bottom of said gas-liquid scrubbing section of step B) constitutes the supply for said distillation section of step B), the liquid effluent obtained from step A) then being directly supplied to step D) for the elimination of liquid impurities and brown oils. This latter embodiment is rendered possible by the process of the invention because the liquid effluent obtained from step A) contains little butadiene.

Said supply is treated in said distillation section of step B) in order to separate an overhead effluent vapour comprising the majority of the butadiene, termed the unrefined butadiene effluent, and an ethanol/acetaldehyde/water residue from the bottom. The term "majority" means more than 80% of the butadiene comprised in the supply to said distillation section, preferably more than 90%, more preferably more than 95%, still more preferably more than 98%, highly preferably more than 99% and highly advantageously all of the butadiene comprised in said supply. This ethanol/acetaldehyde/water residue comprises unreacted ethanol and acetaldehyde and also comprises the water produced and the by-products formed in step A) such as, for example, diethyl ether and ethyl acetate and brown oils. Said ethanol/acetaldehyde/water residue is then supplied to steps D) and E) for the treatment of the effluents. Said distillation section is operated at a pressure in the range 0.1 to 1 MPa, preferably in the range 0.2 to 0.5 MPa.

The arrangement of the recycles and the use of external streams (ethanol feed, water) of the invention, and in particular a cooled ethanol stream, means that the flow rate of the spent water effluent can be minimized, along with the flow rate to be treated by said sections C) and E). The process of the invention can thus be used to minimize the flow rate of the effluents to be treated in the effluent treatment step.

Step C) for Scrubbing Gaseous by-Products with Water

In accordance with the invention, a step C) for scrubbing gaseous by-products with water is supplied with the effluent of gaseous by-products obtained from step B) as well as with a fraction of the water-rich effluent obtained from said step E), and produces at least one alcohol-containing water effluent.

The aim of said step C) is to recover the small fraction of ethanol entrained in said effluent of gaseous by-products obtained from step B) in order to improve the overall yield of the process.

The quantity of water obtained from said step E) which is necessary in said step C) in accordance with the invention is very low, in contrast to that necessary in the prior art, because the effluent vapour obtained from step A) has been scrubbed with an ethanol stream containing little or no acetaldehyde in step B). Thus, only a small fraction of ethanol remains in this stream, which is readily recovered with a small quantity of water compared with the quantity of water which would have been necessary if there had been traces of acetaldehyde in the effluent of gaseous by-products obtained from step B).

The ethanol-charged water following scrubbing is withdrawn from said step C) and constitutes the alcohol-containing water effluent. It is supplied to step E), directly to the water-ethanol distillation section without overloading the acetaldehyde distillation section. In another embodiment of the invention, it is supplied to step D) for the elimination of impurities and brown oils.

Thus, the process of the invention can be used to minimize the flow rate of effluents to be treated in the effluent treatment step. It can also be used to reduce the losses of butadiene as far as possible, allowing more than 98%, preferably more than 99% of the butadiene produced at the end of the reaction steps to be recovered in said purified butadiene effluent.

Step D) for Elimination of Liquid Impurities and Brown Oils

In accordance with the invention, a step D) for elimination of impurities and brown oils is supplied with at least the ethanol/acetaldehyde/water effluent obtained from step B) and with a fraction of the water effluent obtained from step E) and produces at least one ethanol/acetaldehyde/water raffinate, a light brown oil effluent and a heavy brown oil effluent. Said step D) may also be supplied with the liquid effluent obtained from step A).

Preferably, said step D) comprises at least one scrubbing/back-scrubbing section, a section for distilling light brown oils, and a section for distilling heavy brown oils.

Said preferred scrubbing/back-scrubbing section is supplied at an intermediate point with said ethanol/acetaldehyde/water effluent obtained from step B), advantageously as a mixture with the spent water effluent obtained from step E), the alcohol-containing water effluent obtained from step C) and/or as a mixture with a fraction of the spent water effluent obtained from step F). Optionally and advantageously, the liquid effluent obtained from step A) may also be supplied at an intermediate point to said scrubbing/back-scrubbing section. These effluents are more water-rich than the ethanol/acetaldehyde/water effluent obtained from step B), and so introducing them as a mixture means that the hydrocarbon losses in the raffinate can be limited.

The bottom of said preferred scrubbing/back-scrubbing section is supplied with a hydrocarbon effluent and the head is supplied with a fraction of the water effluent obtained from step E), which does not comprise ethanol and acetaldehyde. The hydrocarbon effluent and the fraction of the water effluent obtained from step E) are supplied at a temperature which is in the range 10° C. to 70° C., preferably in the range 45° C. to 55° C. Said scrubbing/back-scrubbing section produces a hydrocarbon scrub extract overhead which is loaded with a fraction of the impurities and brown oils, and said ethanol/acetaldehyde/water raffinate from the bottom.

Said preferred scrubbing/back-scrubbing section is preferably operated at a pressure in the range 0.1 to 0.5 MPa, preferably in the range 0.2 to 0.4 MPa. Preferably, the water added to carry out the back-scrubbing is such that the water content in the water/ethanol/acetaldehyde raffinate is more than 30% by weight, preferably more than 40% by weight.

In one embodiment, the contact between the two liquid phases in said scrubbing/back-scrubbing section is carried out in a liquid-liquid extractor. Various modes of contact may be envisaged. Non-limiting examples that may be cited are a packed column, a pulsed column or an agitated compartmented column. In another embodiment, contact between the two liquid phases in said scrubbing/back-scrubbing section is carried out in a membrane contactor, or a cascade of membrane contactors. This contact mode is particularly suited to the system being used. In fact, water-ethanol-hydrocarbon mixtures are known to form stable emulsions, which may be problematic in a liquid-liquid extractor. The membrane contactor can be used to generate a large contact area, promoting the transfer of impurities and oils towards the hydrocarbon phase without generating an emulsion.

Said hydrocarbon scrub extract is preferably supplied to said distillation section for light brown oils, which produces said light brown oil effluent as a distillate, and a hydrocarbon residue comprising the heavy fraction of the brown oils.

Said light brown oil effluent is composed of impurities produced by the reaction step A), principally diethyl ether, ethyl acetate, pentene, isoprene, butanal, vinyl ethyl ether, and also the light fraction of the brown oils. This effluent may be burned off to provide a portion of the heat necessary for the hot oil circuit or for the steam boilers of the process, or distilled to recover a diethyl ether effluent and/or an ethyl acetate effluent, which could be either upgraded or recycled to the reaction section of step A) for re-transformation.

Said hydrocarbon residue essentially contains the hydrocarbons used for scrubbing, but also the heaviest fraction of the brown oils. In order to prevent the heavy brown oil fraction from accumulating by recycling the hydrocarbon effluent to the liquid-liquid extractor, a fraction of said hydrocarbon residue is treated in said heavy brown oils distillation section, consisting of a distillation column, which produces a hydrocarbon distillate essentially composed of hydrocarbons still with a few traces of brown oils and, as a residue, said heavy brown oils effluent preferably comprising more than 80%, preferably more than 85% of hydrocarbons as well as the heaviest brown oils. The fraction of said hydrocarbon effluent sent to said distillation section for the heavy brown oils is preferably in the range 5% to 30% of the total flow rate of said hydrocarbon residue and preferably in the range 10% to 25%. The hydrocarbon distillate is preferably mixed with the fraction of hydrocarbon residue which has not been treated in said heavy oils distillation section in order to form the hydrocarbon effluent supplied to said scrubbing/back-scrubbing section.

Said heavy brown oil effluent, which typically represents in the range 0.1% to 20% of the feed for said heavy brown oils distillation section, preferably in the range 0.3% to 10%, may be burned off in order to provide a portion of the heat necessary for the hot oil circuit or the steam boilers of the process. A makeup of hydrocarbons equivalent to the losses at the bottom of said heavy oils distillation section may be necessary in order to keep the scrubbing flow rate constant. This column is preferably regulated so as to keep the concentration of brown oils in the hydrocarbon recycle loop constant (hydrocarbon effluent/scrubbing hydrocarbon extract loop).

The light and heavy brown oils are preferably eliminated from the process.

The ethanol/acetaldehyde/water effluent obtained from step B) principally comprises ethanol, acetaldehyde, water but also impurities such as diethyl ether, ethyl acetate and brown oils as defined above. These impurities can accumulate if they are returned to the reaction step A) within the acetaldehyde-rich distillation cut and/or the ethanol-rich distillation cut and if they are only partially converted in the reaction section of step A). Step D) can be used to recover a portion of these impurities before the effluent treatment step E), which means that demixing of the brown oils in the distillation columns can be avoided, the distillation layout can be simplified, and an ethanol effluent, an acetaldehyde/ethanol effluent and a water effluent with a greater purity than in the prior art may be obtained from step E).

Scrubbing the ethanol/acetaldehyde/water effluent obtained from step B) in the preferred scrubbing/back-scrubbing section with a hydrocarbon effluent entrains the brown oils and some impurities, while back-scrubbing the hydrocarbon stream limits any loss of acetaldehyde and ethanol.

Surprisingly, the Applicant has discovered that it is possible to obtain a liquid-liquid phase separation by adding certain hydrocarbons to the ethanol/acetaldehyde residue obtained from step B). This result is surprising, as the ethanol/acetaldehyde residue obtained from the step is very rich in ethanol and acetaldehyde which are miscible with hydrocarbons in any proportions. By suitable selection of the hydrocarbon, the Applicant has discovered that it is possible to obtain liquid-liquid phase separation, and thus to carry out a liquid-liquid extraction in order to eliminate a portion of the impurities contained in the ethanol/acetaldehyde/water effluent obtained from step B). Said hydrocarbon effluent may contain saturated and/or unsaturated and/or aromatic hydrocarbons, preferably saturated hydrocarbons. Said hydrocarbon effluent is advantageously constituted by a mixture of hydrocarbons containing 6 to 40 carbon atoms, preferably in the range 10 to 20 carbon atoms. In a non-limiting manner, said hydrocarbon effluent may be a gas oil cut or desulphurized kerosene cut or alternatively a hydrocarbon cut produced by a Fischer-Tropsch type unit.

Adding water to the preferred scrubbing/back-scrubbing section means that better operation of the process for elimination of the impurities and brown oils in accordance with the invention can be obtained.

Thus, the process of the invention avoids regularly purging ethanol in order to prevent the accumulation of brown oils, which means that the overall performances of the process are improved.

Effluent Treatment Step E)

In accordance with the invention, step E) for the treatment of effluents is supplied with at least the water/ethanol/acetaldehyde raffinate obtained from step D) and produces at least one ethanol effluent, an acetaldehyde effluent and a water effluent. If the spent water effluent obtained from step F) or the alcohol-containing water effluent obtained from step C) has not undergone step D) for the elimination of impurities and brown oils, they may preferably be supplied directly to step E) for the treatment of effluents. Section E) is advantageously also supplied with a fraction of the ethanol feed.

Preferably, and as a distinction from the prior art, no ethanol- or acetaldehyde-losing withdrawal is carried out.

Said step E) comprises at least two distillation sections, a section for the distillation of water and ethanol, and an acetaldehyde distillation section.

In accordance with a first preferred embodiment, said water/ethanol/acetaldehyde raffinate obtained from step D) and optionally the spent water effluent obtained from step F) are supplied to said acetaldehyde distillation section in which the acetaldehyde is separated in a manner so as to form an acetaldehyde effluent, the residue from said acetaldehyde distillation section being supplied to a section for the distillation of water and ethanol in order to separate an overhead ethanol effluent and a bottom water effluent. The alcohol-containing water effluent obtained from step C) does not contain acetaldehyde, and so it is supplied directly to said section for the distillation of water and ethanol. Said section for the distillation of water and ethanol is also advantageously supplied with a fraction of the ethanol feed.

More than 80% by weight, preferably more than 84% by weight of the ethanol effluent obtained from step E) is constituted by ethanol. In a non-limiting manner, the ethanol effluent obtained from step E) may contain impurities such as water, ethyl acetate, butanol and hexanol. The impurities other than water preferably represent less than 10%, more preferably less than 5%, still more preferably less than 2% by weight of said ethanol effluent.

More than 80% by weight, preferably more than 85% by weight of the acetaldehyde effluent obtained from step E) is preferably constituted by acetaldehyde and ethanol. In a non-limiting manner, the acetaldehyde effluent obtained from step E) may contain impurities such as water, ethyl acetate or acetone. The impurities other than water preferably represent less than 10%, preferably less than 5% by weight of said acetaldehyde effluent.

Said acetaldehyde, ethanol and water effluents are then recycled to the remainder of the process of the invention. The fraction of said acetaldehyde effluent supplied to step A) is preferably at least 0.60, more preferably at least 0.65, highly preferably at least 0.70. The fraction of said water effluent supplied to said step C) is advantageously in the range 0 to 0.3, highly advantageously in the range 0 to 0.1, more advantageously in the range 0 to 0.05. The fraction of said water effluent supplied to said step D) for the elimination of impurities and brown oils is advantageously in the range 0 to 1, preferably in the range 0.3 to 0.6, and advantageously in the range 0.45 to 0.55.

In another preferred embodiment of the invention, said acetaldehyde, ethanol and water effluents undergo a purification step before being recycled to the remainder of the process. The term "purification" means bringing said effluents into contact with adsorbents such as activated carbon, silica, alumina or a functionalized polymeric resin, for example. As an example, an activated carbon can be used to eliminate traces of butanol and hexanol comprised in the ethanol effluent. As an example, a basic resin may be used to eliminate acetic acid present in the water effluent. When the adsorbents are saturated, and cannot guarantee the purity of the acetaldehyde, ethanol and water effluents, they are either eliminated or regenerated for re-use.

First Butadiene Purification Step F)

The first butadiene purification step F) comprises at least one gas-liquid scrubbing section the bottom of which is supplied with the unrefined butadiene effluent obtained from B) and the head of which is supplied with a stream of water which may be a stream of water with an origin external to said butadiene production process and/or a fraction of the water effluent obtained from step E), said gas-liquid scrubbing section producing an overhead pre-purified butadiene effluent and a spent water effluent from the bottom. Preferably, said water stream is a stream of water which originates outside the process.

Said spent water effluent contains acetaldehyde and a little butadiene and is preferably sent to the step E) for the treatment of effluents, towards the acetaldehyde distillation section.

The aim of step F) is to eliminate polar impurities, in particular acetaldehyde, which must not be present in the final butadiene in amounts beyond a few ppm. The unrefined butadiene effluent obtained from B) comprises mainly butadiene, but still contains many impurities, including a large quantity of acetaldehyde which forms an azeotrope with the butadiene and thus cannot be completely eliminated by distillation during step B). Thus, the flow rate of said stream of water is adjusted in order to obtain the desired specification for acetaldehyde in the pre-purified butadiene effluent.

Said stream of water is preferably cooled to a temperature below 25° C., preferably below 20° C. before supplying the gas-liquid scrubbing section so as to carry out scrubbing with a reduced quantity of water. The supply temperature for said stream of water is selected so that no hydrates are formed with the butadiene and the light hydrocarbons still present in the unrefined butadiene stream obtained from step B). Said gas-liquid scrubbing section is preferably operated at a pressure such that the butadiene is in the gas phase rather than the liquid phase. The pressure in this section is in the range 0.1 to 1 MPa, preferably in the range 0.2 to 0.3 MPa.

Optional Second Butadiene Purification Step Fbis)

The pre-purified butadiene effluent obtained from step F) advantageously undergoes a second butadiene purification step Fbis) before being supplied to the subsequent butadiene purification step G), said step Fbis) comprising at least one scrubbing section the bottom of which is supplied with said pre-purified butadiene effluent obtained from F), and the head of which is supplied with an absorbent solution. A pre-purified butadiene effluent is withdrawn from the head of said scrubbing section from which traces of acetaldehyde still contained in the pre-purified butadiene effluent have been eliminated, as well as traces of other carbonyls which are less soluble in water than in acetaldehyde such as, for example, butanal, acetone and hexanal, and thus less effectively eliminated by a simple scrub with water. A liquid effluent is withdrawn from the bottom of said scrubbing section which is eliminated from the process.

In a first embodiment of said step Fbis), said absorbent solution is an aqueous solution with a pH of more than 10, adjusted by adding sodium or potassium hydroxide.

In a second embodiment of said step Fbis), said absorbent solution is an aqueous solution of sodium or potassium bisulphite the pH of which is in the range 5 to 8, preferably in the range 6 to 7.

In a third embodiment of said step Fbis), said absorbent solution is an aqueous solution containing a compound from the hydrazine family.

The Applicant has discovered that the combination of steps F) and Fbis) is particularly well suited to the treatment of an unrefined butadiene effluent obtained from a Lebedev type process.

In fact, carrying out step F) alone necessitates large flow rates of water in order to comply with the specification of less than 10 ppm of carbonyl compounds. These large water flow rates are then treated in step E), which entails considerable operating and investment costs. In addition, by very greatly increasing the flow rates of water supplying step F), a small portion of butadiene is dissolved, which reduces the overall yield of the process.

Furthermore, carrying out step Fbis) alone would not be suitable for treating an unrefined butadiene effluent obtained from step B). In fact, the acetaldehyde eliminated from the unrefined butadiene effluent by contact with a basic aqueous solution or a bisulphite solution or an aqueous solution of a compound from the hydrazine family cannot readily be regenerated. As a consequence, a large quantity of acetaldehyde would then be lost, which would lead to a drop in the overall yield of the process.

Thus, the Applicant has identified an optimized and preferred function of the process by concatenating the steps F) and Fbis) of the first and second butadiene purification, meaning that the specifications can be complied with respectively while maximizing the overall yield of the process and minimizing the operating costs.

Subsequent Butadiene Purification Step G)

In accordance with the invention, a subsequent butadiene purification step G) is supplied with at least said pre-purified butadiene effluent obtained from said step F), advantageously treated in the second purification step Fbis), and produces at least one purified butadiene effluent.

This step G) can be used to purify the butadiene produced in the reaction steps to a very high degree of purity (typically more than 99.5% by weight, preferably more than 99.8% by weight and highly preferably more than 99.9% by weight), while limiting the losses of product by separating the impurities which have not or have only partially been removed during steps B), F) and advantageously Fbis).

In a first embodiment of the invention, said step G) comprises at least one drying section, a cryogenic distillation section and a butadiene/butenes separation section using liquid-liquid extraction.

In this embodiment, the pre-purified butadiene effluent obtained from step F), advantageously treated in step Fbis), is supplied to a drying section. This section is intended to comply with the required specifications for water in the final product (purified butadiene effluent) and to allow cryogenic separation to be carried out without the risk of hydrate formation. A dry butadiene effluent is obtained at the outlet from said drying section. The term "dry butadiene" means less than 10 ppm of water, preferably less than 5 ppm, more preferably less than 1 ppm.

Said drying section preferably comprises drying constituted by one or more chambers containing one or more adsorbents with a high affinity for water. In non-limiting manner, this adsorbent may be constituted by silica and/or alumina. In non-limiting manner, this adsorbent may be a zeolite such as zeolite 3A or 4A. When the adsorbent or adsorbents are saturated with water, said pre-purified butadiene effluent is supplied to another chamber containing adsorbent or fresh or regenerated adsorbents.

The adsorbent may be regenerated either by modifying the partial pressure of water in the chamber, or by modifying the temperature in the chamber, or by modifying the partial pressure of water and the temperature in the chamber. In this latter embodiment, regeneration of the water-saturated adsorbent or adsorbents is carried out by heating the chamber, while supplying it with a stream containing little or no water. The term "little or no water" means less than 500 ppm, preferably less than 350 ppm, preferably less than 10 ppm, preferably less than 5 ppm, highly preferably less than 1 ppm. In a non-limiting manner, this stream containing little or no water may be a stream of nitrogen, a stream of air, a stream of hydrocarbon, or a stream of hydrogen.

Said stream containing little or no water is heated to a temperature sufficient to regenerate the adsorbent or adsorbents before being supplied to the chamber containing the adsorbent or adsorbents to be regenerated, preferably to approximately 250° C.

Still in this first embodiment, said dry butadiene effluent is then supplied to a cryogenic distillation section employing a distillation column. The light products are removed from the head of the cryogenic distillation section between −20° C. and −35° C. The column bottom is at a temperature in the range 20° C. to 50° C., preferably between 25° C. and 45° C., highly preferably between 30° C. and 40° C.; the overhead column pressure is in the range 0.3 to 0.4 MPa, preferably 0.35 MPa. The advantage of the column is that it can provide very good separation efficiency for the latter incondensables, without a loss of butadiene (less than 0.05%). Thus, a substantial recycle to step B) and a loss of butadiene are avoided.

The bottom product from said cryogenic distillation section, termed the topped butadiene effluent, comprises butenes as the principal impurity. Said topped butadiene effluent supplies a liquid-liquid butadiene/butenes extraction section such as that described in patent FR 2 036 057.

Still in this first embodiment, said butadiene/butenes separation section is a liquid-liquid extraction section in which said topped butadiene effluent is supplied, at an intermediate zone, to a first liquid-liquid extraction column in which a stream of polar solvent, preferably DMSO, is supplied to the head. The bottom is supplied with a saturated hydrocarbon solvent, preferably pentane or cyclohexane. The flow rates as well as the ratio of the flow rates of the polar solvent to the hydrocarbon solvent are regulated such that the essential part of the butenes will be entrained by the hydrocarbon solvent and the essential part of the butadiene is entrained by the polar solvent.

The butenes/hydrocarbon mixture obtained overhead from the first extraction column is then treated in a first distillation column in order to obtain the butenes effluent overhead and the hydrocarbon solvent from the bottom which may be recycled.

The butadiene/polar solvent mixture is then supplied to the head of a second liquid-liquid extraction column in which the butadiene is extracted from the polar solvent by bringing it into direct contact with a quantity of hydrocarbon solvent that is larger than in the first liquid-liquid extraction column, which is introduced into the bottom of said second liquid-liquid extraction column.

The butadiene/hydrocarbon mixture obtained from the head of the second liquid-liquid extraction column is then treated in a distillation column in order to obtain a purified butadiene effluent overhead and the hydrocarbon solvent from the bottom which may be recycled.

Preferably, the liquid-liquid extraction columns of said butadiene/butenes separation section are operated at a pressure in the range 0.1 to 1 MPa, and at a temperature in the range 20° C. to 60° C.

In another embodiment of the invention, said step G) comprises at least one distillation step and an extractive distillation step. The distillation step may be carried out upstream or downstream of the extractive distillation step. In a non-limiting manner, the extractive distillation may be carried out with a solvent such as N-methyl pyrrolidone, dimethylformamide or acetonitrile.

The various steps for purification of butadiene, B), F), Fbis) and G), may clearly be used to co-treat any stream comprising butadiene which may be produced by other processes located in the proximity of the process of the invention.

Figure 1:
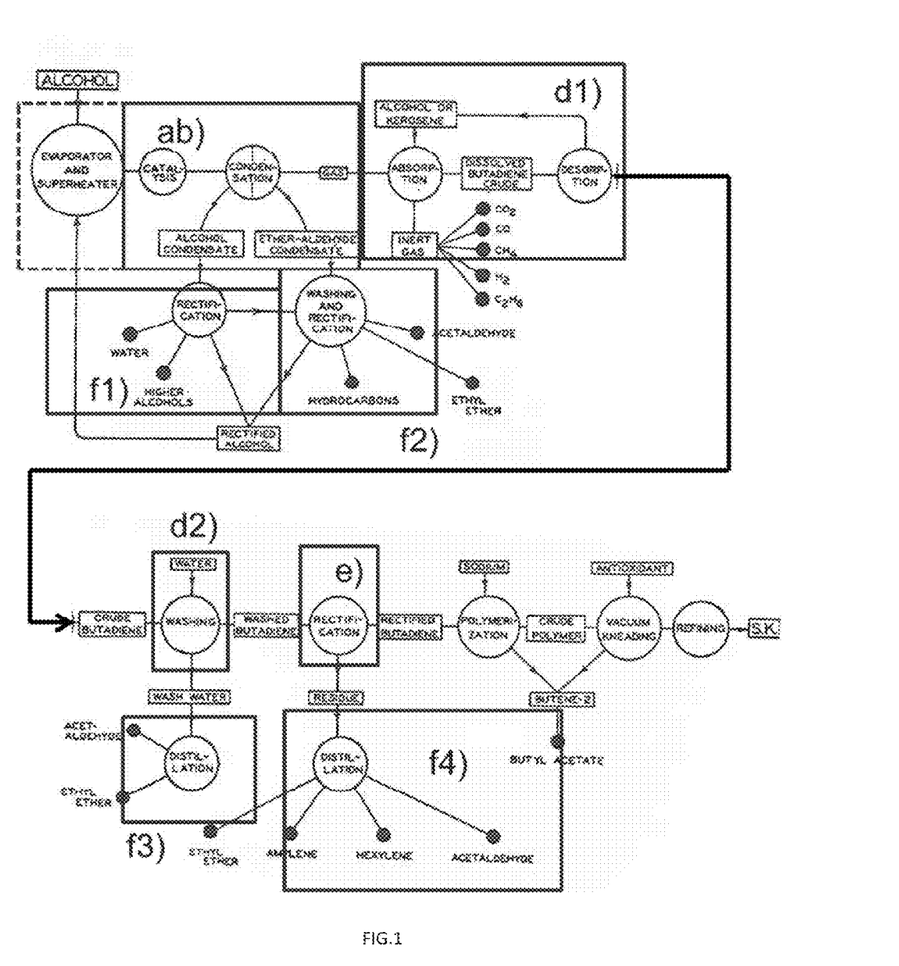
FIG. 1 shows, in a diagrammatic manner, an arrangement of the process of the prior art, based on the work "Synthetic rubber from alcohol", (A. Talalay, M. Magat, 1945).

In FIG. 1, a step ab) for the conversion of ethanol into butadiene is supplied with the ethanol feed comprising ethanol and water, with the ethanol effluent obtained from step f1) and with the acetaldehyde effluent obtained from step f2). Step ab) produces a gaseous effluent, a light liquid effluent and a heavy liquid effluent.

The butadiene extraction step d1) comprises a section for gas-liquid scrubbing with a solvent, and a section for regeneration of solvent by distillation operating in a closed loop. The gas effluent obtained from step ab) is introduced into the bottom of the gas-liquid scrubbing column and the solvent is introduced overhead. The gas-liquid scrubbing column produces an overhead effluent of gaseous by-products and hydrogen and the butadiene-saturated solvent from the bottom, which is sent to an intermediate plate of the distillation column. Said distillation column produces an overhead unrefined butadiene effluent and the regenerated solvent from the bottom which is recycled to the gas-liquid scrubbing column. The solvent may be a hydrocarbon such as, for example, turpentine, or ethanol. The scrubbing solvent is purged in a regular manner and the loop is supplied with fresh solvent.

Step d2) for the first purification of butadiene is supplied with the unrefined butadiene effluent obtained from step d1) and with a water effluent and produces a pre-purified butadiene effluent and a spent water effluent. This step comprises a gas-liquid scrubbing section the bottom of which is supplied with the unrefined butadiene effluent obtained from d1) and with said water effluent overhead. The bottom of the gas-liquid scrubbing column produces said spent water effluent and said pre-purified butadiene effluent is produced overhead.

The subsequent butadiene purification step e) is supplied with said pre-purified butadiene effluent obtained from said step d2) and produces a purified butadiene effluent and a residue. This step includes a distillation.

Step f1) for the treatment of heavy liquid effluent is supplied with the heavy liquid effluent obtained from step ab) and produces a light liquid effluent, a water effluent, an ethanol effluent and a heavy alcohol effluent which is eliminated from the process. This step comprises at least one distillation.

Step f2) for the treatment of the light liquid effluent is supplied with the light liquid effluent obtained from step ab) and with the light liquid effluent obtained from step f1). It produces an acetaldehyde effluent, a diethyl ether effluent and a hydrocarbon effluent and comprises at least one distillation step and a scrubbing section.

Step f3) for the treatment of spent water is supplied with the spent water effluent obtained from step d2) and produces a water effluent, an acetaldehyde effluent and a diethyl ether effluent. It comprises at least one distillation step.

Residue treatment step f4) is supplied with the residue obtained from step e) and produces an acetaldehyde effluent, a diethyl ether effluent, a $C_5$ hydrocarbon effluent and a $C_6$ hydrocarbon effluent which are eliminated from the process. It comprises at least one distillation.

Figure 2:
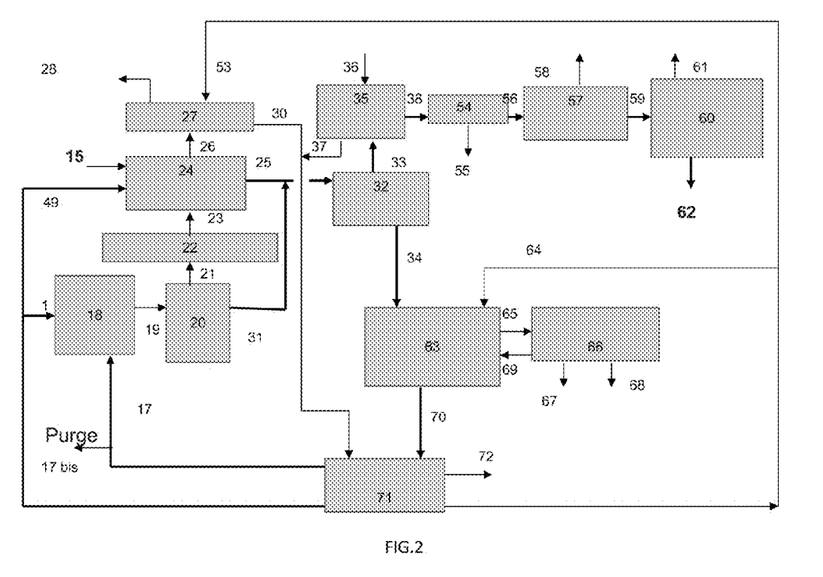
FIG. 2 represents an arrangement of the process of the invention in a diagrammatic and non-limiting manner.

FIG. 2 represents an arrangement of the process of the invention in a diagrammatic and non-limiting manner.

A fraction 1 of the ethanol effluent obtained from the distillation section 71 is sent to the reaction section 18, where a portion of the ethanol is converted principally into acetaldehyde, butadiene and hydrogen. The reaction section 18 is also supplied with the acetaldehyde effluent 17 obtained from the distillation section 71. The conduit 17bis can be used to adjust the flow rate of the effluent 17 supplied to the reaction section 18. The effluent from the reaction section 18 is sent to the separation section 20 via the conduit 19 for separation into a gaseous effluent 21 and a liquid effluent 31.

The gaseous effluent 21 is compressed in the section 22. It is supplied, via the conduit 23, to a scrubbing section 24 in which it is scrubbed by contact with the ethanol feed 15 and recycled ethanol 49. This ensemble is described in more detail in FIG. 3. The compressed and scrubbed gaseous effluent is supplied to a water scrubbing section 27 via the conduit 26, in which section it is scrubbed with a fraction of the water effluent 53 obtained from the distillation section 71. The water charged with ethanol after scrubbing is returned to the distillation section 71 via the conduit 30, directly to the water-ethanol separation column without overloading the acetaldehyde column. The vapour effluent scrubbed in section 27 is withdrawn via the conduit 28.

The liquid effluent 31 obtained from the separator 20 is mixed with the bottom scrubbing liquid 24 arriving via the conduit 25. The mixture is sent to the distillation section 32 which will separate an overhead butadiene cut 33 and a mixture comprising water, ethanol, acetaldehyde and impurities from the bottom. The butadiene cut 33 is sent to a water scrub 35 intended to eliminate polar impurities and especially acetaldehyde. The scrubbing water, which is clean water, is introduced via the conduit 36. Water charged with acetaldehyde is returned to the distillation section 71 via the conduit 37.

The pre-purified butadiene effluent is sent to a drying section 54 via the conduit 38 in order to eliminate all traces of water. The dry butadiene effluent 56 is supplied to a cryogenic distillation step 57 and water is evacuated via the conduit 55. The light products are removed from the cryogenic distillation section overhead at −35° C. via the conduit 58, with a very small loss of butadiene. The topped butadiene cut is removed via the conduit 59 and arrives in a liquid-liquid extraction section 60. The function of this extraction is described in more detail in FIG. 4.

The purified butadiene effluent is removed from this extraction step via the conduit 62, and has a purity that satisfies current specifications (more than 99.5%), the residual impurities being principally butenes. The butenes separated in this section (comprising a small quantity of butadiene) are removed from the unit via the conduit 61.

The ethanol/acetaldehyde residue produced from the bottom of the distillation step 32 is sent via the conduit 34 to the section 63 for scrubbing/back-scrubbing, using heavy hydrocarbons 69 and recycled water 64. The heavy scrubbing hydrocarbons, charged with impurities, are removed via the conduit 65 and supply the regeneration section 66, from which heavy hydrocarbons are removed at 69 and are returned to the scrub, and a light fraction 67 is removed, in particular containing diethyl ether and ethyl acetate, plus some light brown oils. A heavy cut 68 is also removed, containing heavy brown oils and a small portion of the scrubbing hydrocarbons. The function of sections 63 and 66 is described in more detail in FIG. 5.

The bottom liquid from the scrubbing/back-scrubbing section 63, containing both the ethanol/acetaldehyde residue 34 freed from its impurities and with high affinities for the heavy hydrocarbons 69 and the scrubbing water 64, and is sent to the distillation section 71 via the conduit 70. This section can be used to separate an acetaldehyde fraction returned to the reaction section 18 via the conduit 17, an ethanol fraction a portion of which is sent to the reaction section 18 via the conduit 1 and a portion of which is sent to the scrubbing step 24 via the conduit 49, and a water fraction containing a little acetic acid, which is partially recycled to the scrubbing step 27 via the conduit 53 and the scrubbing step 63 via the conduit 64, the remainder of the water being purged from the unit via the conduit 72. The function of this section is described in detail in FIG. 6.

Figure 3:
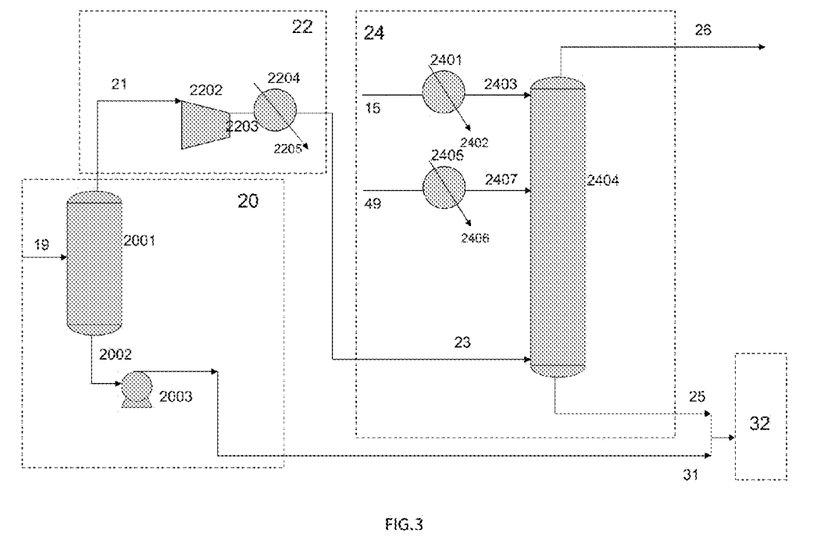
FIG. 3 diagrammatically shows, in a non-limiting manner, separation of the effluent from the reaction section 18 and a portion of the butadiene effluent treatment step.

FIG. 3 diagrammatically shows, in a non-limiting manner, separation of the effluent from the reaction section 18 and a portion of the butadiene effluent treatment step.

The effluent 19 from the reaction section 18 is supplied to a separator 2001 in which a butadiene effluent 21 and a liquid phase 2002 are separated. The butadiene effluent 21 is compressed in a compressor 2202, the compressed vapour effluent 2203 then being cooled in a heat exchanger 2204 by a cooling utility 2205.

The compressed and cooled vapour effluent 23 is supplied to the adiabatic scrubbing column 2404 where it will be scrubbed with the ethanol feed 15 and recycled ethanol 49. The ethanol feed 15 has already been cooled in the heat exchanger 2401 by a coolant arriving via the conduit 2402. The pre-cooled ethanol feed enters the column 2404 via the conduit 2403. The ethanol recycle 49 has already been cooled in the heat exchanger 2405 by a coolant arriving via the conduit 2406. The pre-cooled ethanol feed arrives in the column 2404 via the conduit 2407. A vapour effluent 26 which has been compressed and scrubbed is recovered overhead and the scrubbing liquid 25 is recovered from the bottom.

The bottom scrubbing liquid 25 is mixed with the liquid phase 2002 which has already been pumped via the pump 2003 and is brought in via the conduit 31. The mixture of 25 and 31 contains all of the butadiene produced, and is sent to the section 32.

Figure 4:
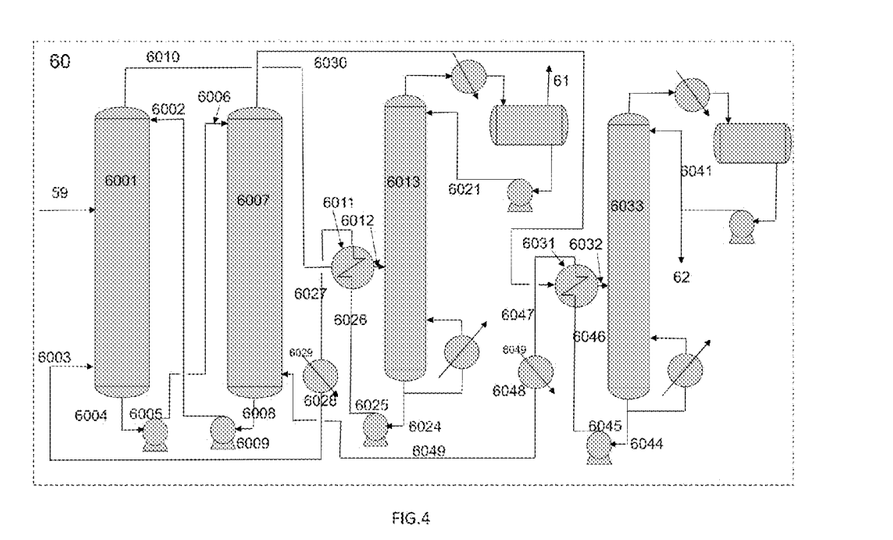
FIG. 4 shows, in a diagrammatic and non-limiting manner, the purification of butadiene using a polar solvent, for example DMSO (dimethylsulphoxide).

FIG. 4 shows, in a diagrammatic and non-limiting manner, the purification of butadiene using a polar solvent, for example DMSO (dimethylsulphoxide).

The dry butadiene effluent is supplied to a first extraction column 6001 via the conduit 59, into which a stream of polar solvent which may, for example, be DMSO, arrives overhead via the conduit 6002. At the bottom, a hydrocarbon solvent such as a pentane or cyclohexane is supplied via the conduit 6003.

At the bottom of the column 6001, the polar solvent and the dissolved butadiene are removed via the conduit 6004, are pumped by the pump 6005, and are sent to the head of the column 6007 via the conduit 6006. A large quantity of hydrocarbon solvent is injected into the bottom of the column 6007 via the conduit 6049 in order to separate the butadiene from the polar solvent. At the bottom of 6007, the polar solvent, free of butadiene, is removed via the conduit 6008 and is pumped via the pump 6009 then returned to the column 6001 via the conduit 6002.

At the column head, the butadiene dissolved in the hydrocarbons is sent to the heat exchanger 6031 via the conduit 6030, where it is heated by indirect exchange with the bottom of the column 6033. At the outlet from the heat exchanger 6031, the butadiene-solvent mixture is supplied to the column 6033 via the conduit 6032.

At the head of the column 6033, after total condensation, a portion of the liquid is sent as a reflux to the column 6033 via the conduit 6041. The remainder, which constitutes the purified butadiene effluent, is sent out of the process via the conduit 62.

The bottom of the column 6033, which is a hydrocarbon solvent, is sent to the pump 6045 via the conduit 6044. At the outlet from the pump 6045, the solvent is sent to a heat exchanger 6031 via the conduit 6046, where it is cooled by indirect heat exchange with the feed from the column 6033. At the outlet from the heat exchanger 6031, the solvent is sent to the heat exchanger 6048 via the conduit 6047, to finish cooling using a cooling utility 6049. At the outlet from the exchanger 6048, the solvent is returned to the scrubbing column 6007 via the conduit 6049.

A mixture of hydrocarbon solvent and butenes is removed from the column 6001 overhead, with a small loss of butadiene. This mixture is sent to the heat exchanger 6011, where it is heated by indirect exchange with the bottom of the column 6013. At the outlet from the heat exchanger 6011, the butene-solvent mixture is supplied to the column 6013 via the conduit 6012. At the head of column 6013, after condensation and gas/liquid separation, the liquid phase is sent as a reflux via the conduit 6021. The vapour phase, essentially constituted by butenes and a little butadiene, is removed from the process via the conduit 61 to act as a fuel, for example.

The bottom of the column 6013, which is a hydrocarbon solvent, is sent to the pump 6025 via the conduit 6024. At the outlet from the pump 6025, the solvent is sent via the conduit 6026 to the heat exchanger 6011, where it is cooled by indirect heat exchange with the feed for the column 6013. At the outlet from the heat exchanger 6011, the solvent is sent via the conduit 6027 to the heat exchanger 6028, to finish cooling using a cooling utility 6029. At the outlet from the exchanger 6028, the solvent is returned to the scrubbing column 6001 via the conduit 6003.

Figure 5:
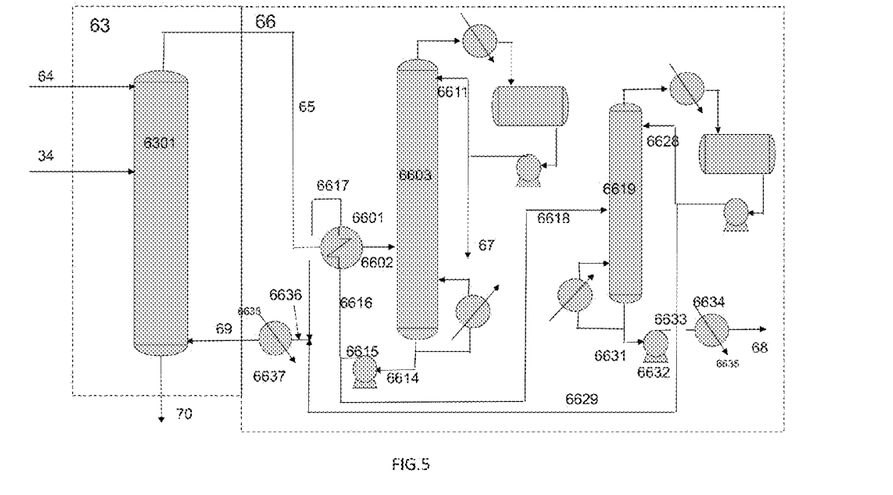
FIG. 5 shows, in a diagrammatic and non-limiting manner, the extraction of less polar impurities and brown oils by scrubbing/back-scrubbing.

FIG. 5 shows, in a diagrammatic and non-limiting manner, the extraction of less polar impurities and brown oils by scrubbing/back-scrubbing.

The ethanol/acetaldehyde residue 34 is supplied to the scrubbing column 6301. The heavy hydrocarbon solvent (which may, for example, be a gas oil cut or desulphurized kerosene, or a cut produced by a Fischer-Tropsch type unit), is supplied to the bottom of the column 6301 via the conduit 69, while a fraction of the water effluent 64 supplies the column 6301 overhead.

The heavy scrubbing hydrocarbon effluent is withdrawn overhead from the column 6301 via the conduit 65 and is preheated in the heat exchanger 6601 by exchange with the bottom of the column 6603. At the outlet from the exchanger 6601, the preheated heavy scrubbing hydrocarbon effluent 6602 is sent to the column 6603.

At the head of column 6603, after condensation, a portion of the liquid is sent as a reflux via the conduit 6611; the remainder is sent out of the unit via the conduit 67.

The column bottom 6603 is sent to the pump 6615 via the conduit 6614. A fraction of the liquid leaving the pump 6615 is sent to another distillation column 6619 via the conduit 6618. The remaining fraction is sent to the heat exchanger 6601 via the conduit 6616, and can be used to cool the bottom liquid 6616 by indirect exchange with the feed 65 for the column 6603. The cooled bottom liquid is removed from the exchanger 6601 via the conduit 6617 for sending to the heat exchanger 6637.

At the head of column 6619, after condensation, a portion of the liquid is sent as a reflux to the column 6619 via the conduit 6628; the remainder is sent to the exchanger 6637 via the conduit 6629 as a mixture with the bottom of the column 6603 where it is cooled with the aid of a cooling utility 6638. The hydrocarbons leaving at 6637 are returned to the scrubbing column 6301 via the conduit 69.

The column head 6619 is essentially composed of heavy hydrocarbons still with a few traces of "black oil". An equivalent makeup of heavy hydrocarbons (not shown) is necessary to keep the scrubbing flow rate constant.

The liquid from the bottom of the column 6619 is removed via the conduit 6631 and is pumped via the pump 6632 then sent via the conduit 6633 to a heat exchanger 6634, where it is cooled by a cooling utility 6635, to be removed from the process via the conduit 68. It can then act as a fuel, for example. The fluid 6635 may be a stream from the unit which has to be reheated.

Figure 6:
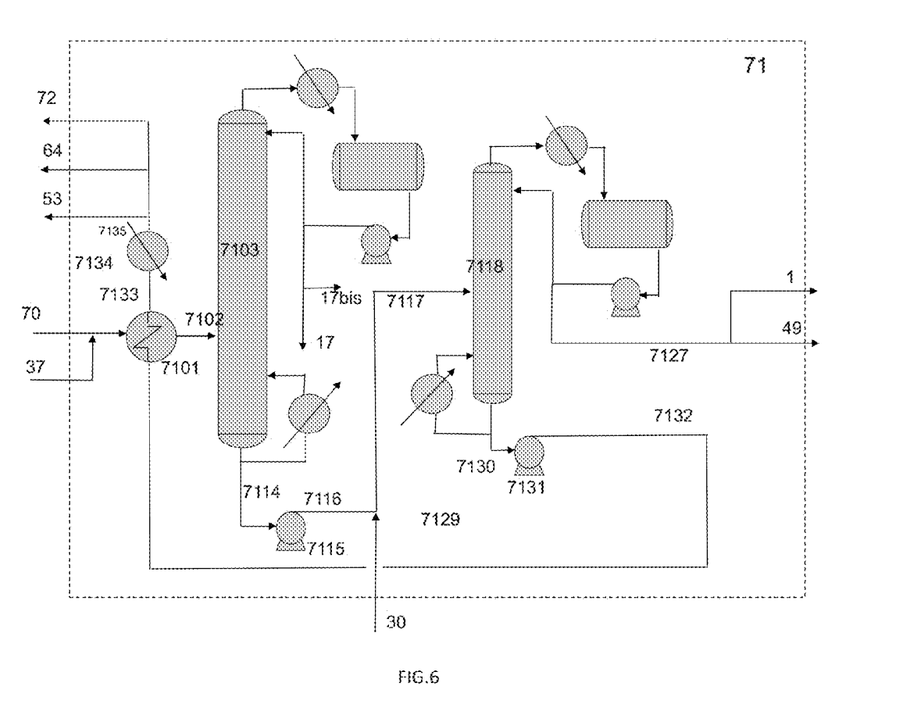
FIG. 6 presents a possible arrangement for the distillation section 71.

FIG. 6 presents a possible arrangement for the distillation section 71.

The ethanol/acetaldehyde/water/polar impurities mixture obtained from scrubbing 63 is supplied to the distillation section 71 via the conduit 70. This stream is mixed with the scrubbing water charged with acetaldehyde arriving from the scrubbing section 35 via the conduit 37. The mixture of these two streams is heated by indirect heat exchange against the stream 7133 in the heat exchanger 7101. The output from this exchanger is supplied to the column 7103 via the conduit 7102. The column head is completely condensed and a distillate (acetaldehyde-rich effluent) is sent towards the reaction section 18 via the conduit 17. A fraction of the distillate is purged via the conduit 17bis. Adjusting the ratio between these two destinations means that the ethanol/acetaldehyde ratio at the inlet to the reactor of section 18 can be adjusted. This distillate principally comprises acetaldehyde, but also water, ethanol and other light impurities (diethyl ether, butanol, acetone, ethyl acetate, etc.).

The product from the bottom of column 7103, principally containing water, ethanol, a little butanol, acetic acid and several other impurities, is removed via the conduit 7114 and then is sent with the aid of the pump 7115 to the column 7118 via the conduit 7116. The scrubbing water from the scrubbing section 27, charged with ethanol, arrives via the conduit 30 and is mixed with the bottom product from 7103 arriving via the conduit 7116. The mixture is sent to the column 7118 via the conduit 7117.

The column head 7118 is completely condensed and a distillate is sent via the conduit 7127, a portion of which being sent to the reaction section 18 via the conduit 1, the other portion towards the scrub 24 via the conduit 49 (ethanol-rich effluent). This distillate principally comprises ethanol, but also water, a little butanol, and several other impurities.

The bottom product from the column 7118 (water-rich effluent), principally containing water and a little acetic acid, is removed via the conduit 7130 and is sent with the aid of the pump 7131 to the heat exchanger 7101 via the conduit 7132, where it is cooled by indirect exchange with the feed for the column 7103. The product is removed from 7101 via the conduit 7133 and is cooled in the exchanger 7134 with the aid of a cooling utility 7135. At the outlet from the exchanger, a portion of the water is sent via the conduit 64 to the scrubbing step 63 and via the conduit 53 to the scrubbing step 27; the remainder is purged out of the unit via the conduit 72.

Example—Process for the Production of Butadiene in Accordance with the Invention The following example is based on process simulations using stream recycles and integrating thermodynamic data based on experimental points (binary liquid-vapour equilibrium data and liquid-liquid distribution coefficient). The flow rate of the feed was adjusted so as to obtain an annual production of 150 kt/year of a butadiene with a purity in the range 99.5% to 100% by weight (consistent with current use of the product), with an annual operating period for the process of 8000 h. Details are provided below of the function of certain steps of the process of the invention.

1.1—Butadiene Extraction Step, Alternative 1

In this arrangement, the vapour effluent from the butadiene conversion step was compressed then scrubbed by contact with the ethanol feed for the conversion process and with recycled ethanol. The effluent gas leaving the scrubbing section formed the scrubbed gas effluent.

Said ethanol feed had the following composition: 93.3% by weight of ethanol and 6.7% of water, with no measurable traces of impurities; it was supplied to the scrubbing column at a temperature of 14° C.; the flow rate of the feed was 63 t/h. The second stream supplied to the scrubbing column was a stream of recycled ethanol (containing 84% of ethanol, the remainder being water), also cooled to 14° C., with a flow rate for this stream of 130 t/h. This scrub was used in order to recover 99.93% of the butadiene comprised in said vapour effluent. The scrubbed gas effluent was free of acetaldehyde, in contrast to prior art examples.

The scrubbed gas effluent was then scrubbed with recycled water in order to recover the ethanol. It was necessary to use 14 t/h of water to recover all of the ethanol.

1.2—Butadiene Extraction Step, Alternative 2

This arrangement differed from the preceding arrangement in that the ethanol feed and the ethanol recycle stream were pre-cooled to −10° C. before being used to scrub the pre-compressed vapour effluent from the butadiene conversion step. In this variation, the flow rate of the feed was identical, but in contrast the flow rate of recycled ethanol was 78 t/h. In fact, because the separation is more efficient at lower temperatures, the recycled ethanol flow rate was reduced, from 130 to 78 t/h. This scrub was used to recover all of the butadiene (100%) included in said vapour effluent.

The scrubbed gas effluent, free of acetaldehyde, was then washed with the recycled water in order to recover the ethanol. It was necessary to use 3.7 t/h of water to recover all of the ethanol.

Cooling the ethanol feed and recycling meant that the flow rate of recycled ethanol was reduced, reducing the feed in all of the equipment of the process layout. In addition, the flow rate of water required for washing was also reduced (divided by 3.8), which meant that 11% of the flow rate of the water at the inlet to the effluent treatment step could be reduced, which as a consequence reduces the dimensions of the separation equipment and its energy consumption.

1.3—Butadiene Extraction Step, Alternative 3

In this arrangement, the vapour effluent from the butadiene conversion step was compressed then scrubbed by contact with only an ethanol effluent obtained from the effluent treatment step. The gas effluent at the scrub outlet formed the scrubbed gas effluent.

Said ethanol effluent obtained from the step for the treatment of the effluents had the following composition: 84% by weight of ethanol and 16% of water, with no measurable traces of impurities. It was supplied to the scrubbing column at a temperature of −10° C. and at a flow rate of 207 t/h. This scrub was used to recover all of the butadiene included in said vapour effluent. The scrubbed gas effluent was free of acetaldehyde, in contrast to the prior art case.

The scrubbed gas effluent was then scrubbed with recycled water in order to recover the ethanol. It was necessary to employ 8.1 t/h of water in order to recover all of the ethanol.

This arrangement should be compared with arrangement 1.2 above. It should be noted that the invention as implemented in arrangement 1.2, using the ethanol feed and a complement of recycled ethanol effluent, can be used to reduce the flow rate of the ethanol stream scrubbing the butadiene cut by 8% compared with using only an ethanol effluent obtained from the effluent treatment step. This saving contributes directly to reduced investment and operating costs. In addition, the flow rate of water necessary for the recovery of butadiene is divided by 2, which relieves the distillation columns of investment costs and operating costs.

1.4—Subsequent Butadiene Separation Step G)

The purified butadiene effluent obtained from the first butadiene purification step was supplied to a drying section by passing it in succession over an alumina, then over a zeolite 4A, in order to scrub all of the water which might have been present in said purified butadiene effluent. The effluent from the drying section formed the dry butadiene effluent. This dry butadiene effluent was then supplied to a cryogenic distillation column operated at an overhead pressure of 0.35 MPa, a bottom temperature of 35° C. and an overhead temperature of −23° C.

Finally, the distillation residue, known as the topped butadiene effluent, was supplied to a liquid-liquid extraction section using DMSO and cyclohexane.

A first scrubbing column was supplied overhead with 252 t/h of DMSO and at the bottom with 50 t/h of cyclohexane. This first column comprised 20 theoretical scrubbing stages.

The bottom product from the first column was sent to a second scrubbing column comprising 10 theoretical stages.

The overhead product from this second scrubbing column was treated in a distillation column, which meant that the butadiene could be separated from the cyclohexane; it comprised 24 theoretical stages and operated with a reflux ratio of 8.3.

The overhead product from the first scrubbing column was treated in a distillation column in order to separate the butenes from cyclohexane; it comprised 26 theoretical stages and operated with a reflux ratio of 10.

99.68% of the butadiene entering the second butadiene separation step was recovered as a product with a purity of 99.68% by weight.

A purified butadiene effluent was obtained from the outlet from the liquid-liquid extraction section for which the butadiene content was 99.68% by weight. The butadiene losses over all of the purification steps (calculated from the ratio of the flow rate of pure butadiene included in the purified butadiene effluent over the flow of pure butadiene included in the effluent from the butadiene conversion reactor) was less than 0.7% by weight.

The arrangement of the steps and recycles of the invention, in particular by preventing the accumulation of impurities, meant that almost all of the compounds which had not reacted could be recycled. Thus, despite a low conversion per pass in the reactors, comparable with the prior art, the overall yield was improved by more than 10 points compared with the prior art, with a $t_{butadiene\ produced}$ per $t_{converted\ ethanol}$ yield of 36.8% and a recovery and upgrade of 99.9% of the ethanol comprised in the feed for the process.

The invention claimed is:

1. A process for the production of butadiene from an ethanol feed comprising at least 80% by weight of ethanol, said process comprising at least:
   A) converting the ethanol into butadiene, comprising reacting at least the ethanol effluent and a fraction of acetaldehyde effluent obtained from E), at a pressure in the range 0.1 to 1.0 MPa and at a temperature in the range 300° C. to 400° C. in the presence of a catalyst, separating the effluent from said reaction into at least a gaseous effluent and a liquid effluent, the fraction of the acetaldehyde effluent obtained from E) which is not supplied to said reaction constituting a purge stream;
   B) extracting butadiene, by compressing said gaseous effluent obtained from A) to a pressure in the range 0.1 to 1.0 MPa, gas-liquid scrubbing of said compressed gaseous effluent with an ethanol stream comprising said ethanol feed for the process and/or a fraction of the ethanol effluent obtained from E) in which the gas is supplied at a temperature in the range 10° C. to 60° C., and the liquid is supplied at a temperature in the range 20° C. to −30° C., and producing at least one ethanol stream enriched in butadiene and a gaseous effluent of by-products, distilling said ethanol stream enriched in butadiene and producing an unrefined butadiene effluent and an ethanol/acetaldehyde/water residue, said distillation being operated at between 0.1 and 1 MPa;
   C) scrubbing gaseous by-products with water supplied with the effluent of gaseous by-products obtained from B), as well as with a fraction of the water-rich effluent obtained from E) and producing at least one alcohol-containing water effluent;
   D) eliminating impurities and brown oils, in at least the ethanol/acetaldehyde/water effluent obtained from B), with a fraction of the water effluent obtained from step E), and producing at least one water/ethanol/acetaldehyde raffinate, a light brown oil effluent and a heavy brown oil effluent;

E) effluent treatment of at least the water/ethanol/acetaldehyde raffinate obtained from D), producing at least one ethanol effluent, an acetaldehyde effluent and a water effluent;

F) a first butadiene purification comprising at least one gas-liquid scrubbing section the bottom of which is supplied with the unrefined butadiene effluent obtained from B) and the head of which is supplied with a stream of water which is a stream of water with an origin external to said butadiene production process and/or a fraction of the water effluent obtained from E), said scrubbing section producing an overhead pre-purified butadiene effluent and a spent water effluent from the bottom;

G) a subsequent butadiene purification of at least said pre-purified butadiene effluent obtained from said F), and producing at least one purified butadiene effluent.

2. A process according to claim 1, in which the pre-purified butadiene effluent obtained from F) undergoes a second butadiene purification Fbis) before being supplied to the subsequent butadiene purification G), said Fbis) comprising at least one scrubbing section the bottom of which is supplied with said pre-purified butadiene effluent obtained from F), and the head of which is supplied with an absorbent solution.

3. A process according to claim 2, in which said absorbent solution is an aqueous solution with a pH of more than 10, adjusted by adding sodium or potassium hydroxide.

4. A process according to claim 2, in which said absorbent solution is an aqueous sodium or potassium bisulphite solution the pH of which is in the range 5 to 8.

5. A process according to claim 2, in which said absorbent solution is an aqueous solution containing a hydrazine compound.

6. A process according claim 1, in which D) comprises at least one scrubbing/back-scrubbing section, a section distilling light brown oils, and a section distilling heavy brown oils, said scrubbing/back-scrubbing section being supplied at an intermediate point with said ethanol/acetaldehyde/water effluent obtained from B), at the bottom with a hydrocarbon effluent and overhead with a fraction of the water effluent obtained from E) and producing at least one hydrocarbon scrubbing extract and an ethanol/acetaldehyde/water raffinate, said light brown oil distillation being supplied with said hydrocarbon scrubbing extract and producing, as a distillate, a light brown oil effluent, and a hydrocarbon residue, said heavy oils distillation section being supplied with a fraction in the range 5% to 30% of the total flow rate of said hydrocarbon residue and producing a hydrocarbon distillate and, as a residue, a heavy brown oil effluent, said hydrocarbon distillate and the untreated fraction of said hydrocarbon residue being mixed in order to constitute the hydrocarbon effluent supplying said scrubbing/back-scrubbing section.

7. A process according to claim 1, in which said reaction A) is also supplied with a fraction of said ethanol feed.

8. A process according to claim 1, in which A) is also supplied with an external acetaldehyde stream.

9. A process according to claim 1, in which the purge stream of A) is transformed in a dedicated hydrogenation in order to produce ethanol which will then be sent to said reaction A).

10. A process according to claim 1, in which the ethanol stream enriched in butadiene withdrawn from the bottom of said gas-liquid scrubbing B) is mixed with liquid effluent obtained from A) in a manner such as to form the supply for said distillation of B).

11. A process according to claim 1, in which the ethanol stream enriched in butadiene withdrawn from said gas-liquid scrubbing B) is the supply for said distillation B), the liquid effluent obtained from A) then being directly supplied to D) eliminating liquid impurities and brown oils.

12. A process according to claim 6, in which said scrubbing/back scrubbing section of said D) is supplied with said ethanol/acetaldehyde/water effluent obtained from B), at an intermediate point, as a mixture with the spent water effluent obtained from E), the alcohol-containing effluent obtained from C) and/or as a mixture with a fraction of the spent water effluent obtained from F).

13. A process according to claim 1, in which E) is also supplied with a fraction of the ethanol feed.

14. A process according to claim 1, in which G) comprises drying, cryogenic distillation and butadiene/butenes separation by liquid-liquid extraction.

15. A process according to claim 1, in which G) comprises at least one distillation and an extractive distillation.

* * * * *